(12) United States Patent
Manthei et al.

(10) Patent No.: US 11,103,467 B2
(45) Date of Patent: *Aug. 31, 2021

(54) METHOD FOR TREATING DEPRESSION

(71) Applicant: DEVELCO PHARMA SCHWEIZ AG, Pratteln (CH)

(72) Inventors: Sascha Manthei, Pratteln (CH); Helene Rey, Pratteln (CH); Marc Fischer, Pratteln (CH); Olaf Mundszinger, Pratteln (CH)

(73) Assignee: Develco Pharma Schweiz AG, Pratteln (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/437,467

(22) Filed: Jun. 11, 2019

(65) Prior Publication Data

US 2019/0290600 A1 Sep. 26, 2019

Related U.S. Application Data

(62) Division of application No. 15/304,613, filed as application No. PCT/EP2015/058318 on Apr. 16, 2015, now Pat. No. 10,335,379.

(30) Foreign Application Priority Data

Apr. 17, 2014 (EP) ..................... 14165057

(51) Int. Cl.
| | |
|---|---|
| *A61K 31/135* | (2006.01) |
| *A61K 9/20* | (2006.01) |
| *A61K 9/50* | (2006.01) |
| *A61K 9/00* | (2006.01) |

(52) U.S. Cl.
CPC .......... *A61K 31/135* (2013.01); *A61K 9/0053* (2013.01); *A61K 9/2013* (2013.01); *A61K 9/2077* (2013.01); *A61K 9/2081* (2013.01); *A61K 9/5078* (2013.01)

(58) Field of Classification Search
None
See application file for complete search history.

(56) References Cited

U.S. PATENT DOCUMENTS

| | | | |
|---|---|---|---|
| 3,723,614 A | 3/1973 | Langauer | |
| 6,194,000 B1 | 2/2001 | Smith et al. | |
| 10,335,379 B2 * | 7/2019 | Manthei | ............... A61K 31/135 |
| 2008/0268071 A1 | 10/2008 | Gant et al. | |
| 2014/0079740 A1 | 3/2014 | Salama | |

FOREIGN PATENT DOCUMENTS

| | | |
|---|---|---|
| DE | 10 2007 009 888 A1 | 9/2008 |
| EP | 1 103 256 A1 | 5/2001 |

OTHER PUBLICATIONS

Serafini et al., "The Role of Ketamine in Treatment-Resistant Depression: A Systematic Review," Current Neuropharmacology, 2014, 12, 444-461. (Year: 2014).*

* cited by examiner

*Primary Examiner* — Aradhana Sasan
(74) *Attorney, Agent, or Firm* — Jason D. Voight

(57) ABSTRACT

A method for treating depression in patients with depression and bipolar disorder who have not responded to antidepressants and to avoid dose dumping upon ingestion of alcohol. The present invention also relates to an oral dosage form for administration of ketamine and a method of preparing an oral dosage form for administration of ketamine, preferably once or twice a day.

16 Claims, 2 Drawing Sheets

METHOD FOR TREATING DEPRESSION

This is a divisional of application Ser. No. 15/304,613 which is the National Stage of International Application PCT/EP2015/058318 filed Apr. 16, 2015, which is hereby incorporated in its entirety by reference herein.

Ketamine can be effective in treating depression in patients with depression and bipolar disorder who have not responded to antidepressants. It produces a rapid antidepressant effect, as opposed to the several weeks taken by typical antidepressants to work.

The present invention relates to an oral dosage form of ketamine and a method of preparing said oral dosage form. The dosage form can be used in the treatment of neuropathic pain, preferably once or twice a day.

Ketamine is a drug used in human and veterinary medicine, primarily for the induction and maintenance of general anesthesia, usually in combination with a sedative. Other uses include sedation in intensive care, analgesia, and treatment of bronchospasm. Ketamine has a wide range of effects in humans, including analgesia, anesthesia, hallucinations, elevated blood pressure, and bronchodilation. Like other drugs of its class, such as tiletamine and phencyclidine (PCP), ketamine induces a state referred to as "dissociative anesthesia" and is used as a recreational drug. Ketamine hydrochloride is sold as Ketanest®, Ketaset®, and Ketalar®. Pharmacologically, ketamine is classified as an N-methyl-D-aspartate (NMDA) receptor antagonist.

Ketamine can also be effective in treating neuropathic pain. Neuropathic pain is pain caused by damage or disease that affects the somatosensory system. It may be associated with abnormal sensations called dysesthesia, and pain produced by normally non-painful stimuli (allodynia). Neuropathic pain may have continuous and/or episodic (paroxysmal) components.

Central neuropathic pain is found in spinal cord injury, multiple sclerosis, and some strokes. Aside from diabetes and other metabolic conditions, the common causes of painful peripheral neuropathies are herpes zoster infection, HIV-related neuropathies, nutritional deficiencies, toxins, remote manifestations of malignancies, immune mediated disorders and physical trauma to a nerve trunk. Neuropathic pain is common in cancer as a direct result of cancer on peripheral nerves (e.g., compression by a tumor), or as a side effect of chemotherapy, radiation injury or surgery.

At subanesthetic doses, ketamine produces a dissociative state, characterised by a sense of detachment from one's physical body and the external world which is known as depersonalization and derealization. At sufficiently high doses, users may experience what is called the "K-hole", a state of extreme dissociation with visual and auditory hallucinations.

A problem connected to analgesics and opioid analgesics is the so-called dose dumping. Dose dumping is a phenomenon that occurs, for instance, when patients do no comply with the advice to avoid the intake of alcohol concomitantly with the administration of the controlled release pharmaceutical dosage form. The intake of alcohol can accelerate dramatically the release of the active ingredient, thus leading to potentially very harmful consequences for the patient, in particular in case of analgesics and opioid analgesics. Further, the accelerated release of the active ingredient by means of alcohol for example is often also a desired process for people aiming at a hallucinogenic experience caused by a high dose of the drug, thus leading to drug abuse.

It is therefore desirable to provide dosage forms that can minimize dose dumping and drug abuse.

Further, the possibility to form controlled release dosage forms of ketamine is described in the prior art. However, no specific controlled release composition or formulation comprising ketamine is known in the prior art. EP 1 103 256 A1 describes the use of ketamine in treating neuroendocrine immune dysfunction or algogenic psychosyndrome. The ketamine can be administered orally, e.g. as a controlled release dosage form. WO 2008/134525 A1 is directed to deuterium labelled ketamine and pharmaceutical compositions thereof, also comprising release-controlling agents.

DE 10 2007 009 888 A1 describes the use of S-(+)-ketamine for treating depressions. It discloses i.a. its oral administration, without specifying the composition or addressing the dose dumping problem and/or drug abuse problem.

No specific controlled release composition or formulation comprising ketamine is described in the prior art and no controlled release formulation of ketamine has been marketed, but only ketamine formulations for parenteral administration, such as Ketanest, Ketaset and Ketalar, as no satisfactory in vivo plasma level of ketamine could be achieved with oral formulations.

It is therefore an object of the present invention to provide an oral dosage form of ketamine which provides a satisfactory in vivo plasma level of ketamine and at the same time prevents dose dumping and drug abuse.

The inventors of the present invention have now surprisingly found that very advantageous in vivo properties can be achieved by an oral dosage form comprising ketamine, which provides a specific in vitro release of ketamine.

Hence, one aspect of the present invention is the provision of an oral dosage form comprising ketamine or a pharmaceutically acceptable salt or solvate thereof. In a first embodiment of the invention the dosage form provides an in vitro release of ketamine of 0 to 40% after 2 hours, of 10 to 70% after 4 hours, of 30 to 85% after 6 hours and of 45 to 100% after 8 hours, when measured according to the USP Basket Method I in 0.1M HCl at 100 rpm and 37° C.

In a preferred embodiment, the in vitro release of ketamine is 5 to 30%, preferably 8 to 25% after 2 hours, 20 to 60% after 4 hours, 45 to 80% after 6 hours and 60 to 99% after 8 hours, when measured according to the USP Basket Method I in 0.1M HCl at 100 rpm and 37° C.

A second aspect of the invention is a modified release oral dosage form comprising ketamine or a pharmaceutically acceptable salt or solvate thereof, wherein the ratio of the amount of ketamine released after 1 hour of in-vitro dissolution of the dosage form at 37° C. in a aqueous solution containing 20% by volume of ethanol to the amount of ketamine released after 1 hour of in-vitro dissolution of the dosage form at 37° C. in an ethanol-free aqueous solution is less than 2:1, preferably less than 1.7:1, more preferably less than 1.5:1, most preferably less than 1.2:1, when measured according to the USP 1 Basket Method in 0.1M HCl at 100 rpm.

Hence, the dosage forms of the present invention have proven advantageous to avoid the effect of so-called dose dumping. It has been found that the use of the dosage forms of the present invention is a very effective means to avoid or at least significantly reduce the risk of dose dumping upon ingestion of alcohol.

As used herein for all in vitro release measurements, the USP Basket Method I is carried out in 500 ml liquid for ketamine amounts of less than or equal to 10 mg and in 1000 ml liquid for ketamine amounts of more than 10 mg. If ketamine is used as free base, the amount of 10 mg refers to the weight of the free base. If ketamine is used in the form of a pharmaceutical acceptable salt or solvate, the amount of 10 mg refers to the weight of the salt or solvate.

"Ketamine" as used herein is understood to comprise the compound of formula (I)

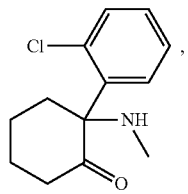

(I)

having the IUPAC name 2-(2-chlorophenyl)-2-(methylamino)cyclohexan-1-one. Accordingly, ketamine comprises the R and S enantiomers as well as pharmaceutically acceptable salts or solvates thereof. In one embodiment, ketamine is (R)-ketamine or pharmaceutically acceptable salts or solvates thereof. In another embodiment, ketamine is (S)-ketamine or pharmaceutically acceptable salts or solvates thereof. In a further embodiment, ketamine is a racemate of (S)-ketamine and (R)-ketamine or pharmaceutically acceptable salts or solvates thereof, or any mixture of (S)-ketamine and (R)-ketamine or pharmaceutically acceptable salts or solvates thereof. Ketamine can preferably comprise the pharmaceutically acceptable acid addition salts thereof. The acids which are used to prepare the pharmaceutically acceptable acid addition salts are preferably those which form non-toxic acid addition salts, i.e. salts containing pharmacologically acceptable anions, such as chloride, bromide, iodide, nitrate, sulfate, bisulfate, phosphate, acid phosphate, acetate, lactate, citrate, (D,L)- and L-tartrate, (D,L)- and L-malate, bitartrate, succinate, maleate, fumarate, gluconate, saccharate and benzoate. A preferred salt is the hydrochloride of ketamine.

Ketamine as used herein can also comprise its metabolites. The metabolite is norketamine or dehydronorketamine, preferably norketamine Norketamine has the IUPAC name 2-amino-2-(2-chlorophenyl)cyclohexan-1-one of formula (II)

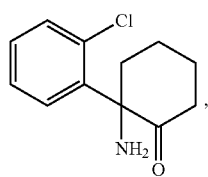

(II)

and is obtained from ketamine through N-demethylation. Norketamine can be provided as (R)-norketamine or pharmaceutically acceptable salts or solvates thereof, or (S)-norketamine or pharmaceutically acceptable salts or solvates thereof, racemate of (S)-norketamine and (R)-norketamine or pharmaceutically acceptable salts or solvates thereof, or any mixture of (S)-norketamine and (R)-norketamine or pharmaceutically acceptable salts or solvates thereof. Dehydronorketamine has the IUPAC name 6-amino-6-(2-chlorophenyl)cyclohex-2-en-1-one of formula (III)

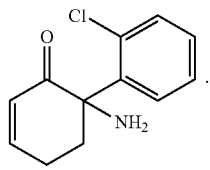

(III)

Dehydronorketamine can be provided as (R)-dehydronorketamine or pharmaceutically acceptable salts or solvates thereof, or (S)-dehydronorketamine or pharmaceutically acceptable salts or solvates thereof, racemate of (S)-dehydronorketamine and (R)-dehydronorketamine or pharmaceutically acceptable salts or solvates thereof, or any mixture of (S)-dehydronorketamine and (R)-dehydronorketamine or pharmaceutically acceptable salts or solvates thereof. Norketamine and dehydronorketamine can preferably comprise the pharmaceutically acceptable acid addition salts thereof. The acids which are used to prepare the pharmaceutically acceptable acid addition salts are preferably those which form non-toxic acid addition salts, i.e. salts containing pharmacologically acceptable anions, such as chloride, bromide, iodide, nitrate, sulfate, bisulfate, phosphate, acid phosphate, acetate, lactate, citrate, (D,L)- and L-tartrate, (D,L)- and L-malate, bitartrate, succinate, maleate, fumarate, gluconate, saccharate and benzoate. A preferred salt is the hydrochloride salt.

The following description of embodiments applies for both aspects of the invention. Further, the first aspect and the second aspect of the invention are not mutually exclusive, i.e. embodiments of the first aspect can at the same time comprise the features of the first aspect and vice versa.

The oral dosage form of the present invention is a modified release dosage form. As used herein, the term "modified release" refers to a dosage form in which the rate or place of release of the active ingredient is different from that of an immediate release dosage form when administered by the same route. Modified release dosage forms can include delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices including, but not limited to, matrix controlled release devices, osmotic controlled release devices, multiparticulate controlled release devices, ion-exchange resins, enteric coatings, multilayered coatings, microspheres, liposomes, and combinations thereof.

In one embodiment of the invention, the oral dosage form is a matrix controlled release dosage form.

In one embodiment, the matrix controlled release dosage form comprises a matrix system, which preferably is swellable, non-swellable, erodible or non-erodible, and preferably comprises polymers, including synthetic polymers, and naturally occurring polymers and derivatives, such as polysaccharides and proteins. In a further embodiment, the dosage form comprises a non-erodible matrix system. Ketamine can be dissolved or dispersed in an inert matrix and is released primarily by diffusion through the inert matrix once administered.

Preferred materials for forming a matrix comprise chitin, chitosan, dextran, and pullulan, gum agar, gum arabic, gum karaya, locust bean gum, gum tragacanth, carrageenans, gum ghatti, guar gum, xanthan gum, and scleroglucan, starches, such as dextrin and maltodextrin, hydrophilic colloids, such as pectin, phosphatides, such as lecithin, alginates, propylene glycol alginate, gelatin, collagen, and cellulosics, such as ethyl cellulose (EC), methylethyl cellulose (MEC), carboxymethyl cellulose (CMC), carboxymethyl ethylcellulose (CMEC), hydroxyethyl cellulose (HEC), hydroxypropyl cellulose (HPC), cellulose acetate (CA), cellulose propionate (CP), cellulose butyrate (CB), cellulose acetate butyrate (CAB), cellulose acetate phthalate (CAP), cellulose acetate trimellitate (CAT), hydroxypropyl methyl cellulose (HPMC), HPMCP, HPMCAS, hydroxypropyl methyl cellulose acetate trimellitate (HPMCAT), and ethylhydroxy ethylcellulose (EHEC), polyvinyl pyrrolidone, polyvinyl alcohol, polyvinyl acetate, fatty acid esters, polyacrylamide, polyacrylic acid, copolymers of ethacrylic acid or methacrylic acid (EUDRAGIT®, Rohm America, Inc., Piscataway, N.J.), poly(2-hydroxyethyl-methacrylate), polylactides, copolymers of L-glutamic acid and ethyl-L-glutamate, degradable lactic acid-glycolic acid copolymers, poly-D-(−)-3-hydroxybutyric acid, and other acrylic acid derivatives, such as homopolymers and copolymers of butylmethacrylate, methylmethacrylate, ethylmethacrylate, ethylacrylate, (2-dimethylaminoethyl)methacrylate, and (trimethylaminoethyl)methacrylate chloride.

Additional materials for forming a matrix device comprise plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinylacetate copolymers, ethylene/propylene copolymers, ethylene/ethyl acrylate copolymers, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, polyvinyl chloride, plasticized nylon, plasticized polyethyleneterephthalate, natural rubber, silicone rubbers, polydimethylsiloxanes, silicone carbonate copolymers; and fatty compounds, such as carnauba wax, microcrystalline wax, and triglycerides such as hydrogenated castor oil. In a preferred embodiment the matrix forming material is hydrogenated castor oil. In another preferred embodiment the matrix forming material is HPMC.

The matrix forming material is preferably present in the dosage form of the invention in a concentration of between 10 and 95 wt.-%, more preferably 20 to 75%, in particular 25 to 65%, based on the total weight of the dosage form.

The dosage form comprising a matrix system may further comprise excipients such as lubricants, fillers, glidants, binders, stabilizers. Regarding preferred embodiments of said excipients it is referred to explanations given below.

In a preferred embodiment the dosage form comprises
10 and 95 wt.-%, more preferably 20 to 75%, in particular 30 to 65% matrix forming material,
0 to 90 wt.-%, preferably 5 to 70 wt. %, more preferably 10 to 50 wt. %, in particular 15 to 30 wt.-% fillers,
optionally 0 to 25 wt.-%, preferably 1 to 20 wt. %, more preferably 5 to 15% binders,
0 to 5 wt.-%, preferably 0.1 to 4 wt. %, more preferably 0.5 to 3% glidants,
0 to 5 wt.-%, preferably 0.1 to 3 wt. %, more preferably 0.3 to 2% lubricants
based on the total weight of the dosage form.

The matrix controlled release dosage form can be prepared by direct-compression, wet-granulation or dry-granulation. Direct compression is a preferred embodiment. For more detailed explanations about the compression step it is referred to the illustrations given below.

In a further embodiment of the invention, the dosage form of the invention can be present in form of an osmotic controlled release device, including one-chamber system (elementary osmotic pump), two-chamber system (push-pull systems), asymmetric membrane technology (AMT), and extruding core system (ECS). Osmotic controlled release devices should comprise cores, for example tablets, comprising ketamine, which are enveloped by a semipermeable membrane which preferably has at least one orifice. The water-permeable membrane is impermeable to the components of the core but permits water to enter the system from outside by osmosis. The water which penetrates in then, through the osmotic pressure produced, releases the active ingredient in dissolved or suspended form from the orifice(s) in the membrane. The total active ingredient release and the release rate can substantially be controlled via the thickness and porosity of the semipermeable membrane, the composition of the core and the number and size of the orifice(s).

In addition to the ketamine, the core of the osmotic device optionally includes an osmotic agent which preferably creates a driving force for transport of water from the environment of use into the core of the device.

In the osmotic two-chamber system, the core consists of two layers, one active ingredient layer and one osmosis layer. The active ingredient layer preferably comprises 1 to 70% ketamine, 30 to 95% of one or more osmopolymers. The osmosis layer preferably comprises 30 to 90% of one or more osmopolymers, 10 to 60% of an osmogen, where the difference from 100% in the individual layers is formed in each case independently of one another by one or more additional ingredients in the form of pharmaceutically usual excipients. The osmogens and osmopolymers used in the core of the osmotic two-chamber system may be as described in the following paragraphs.

In one embodiment, the osmotic agents are water-swellable polymers, which are also referred to as "osmopolymers" and "hydrogels," including hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

In a second embodiment, the osmotic agents are osmogens which are capable of imbibing water to affect an osmotic pressure gradient across the barrier of the surrounding coating. Preferred osmogens comprise water-soluble salts of inorganic or organic acids or nonionic organic substances with a high solubility in water, such as for example carbohydrates, especially sugars, sugar alcohols or amino acids. For example, the osmogens are selected from inorganic salts such as chlorides, sulphates, carbonates and bicarbonates of alkali metals or alkaline earth metals, such as lithium, sodium, potassium, magnesium, calcium, and phosphates, hydrogen phosphates or dihydrogen phosphates, acetates, succinates, benzoates, citrates or ascorbates thereof. It is furthermore possible to use pentoses such as arabinose, ribose or xylose, hexoses such as glucose, fructose, galactose or mannose, disaccharides such as sucrose, maltose or lactose or trisaccharides such as raffinose. The water-soluble amino acids include glycine, leucine, alanine or methionine. Sodium chloride is particularly preferably used according to the invention. The osmogens are preferably present in an amount of 10 to 30% based on the total mass of the core ingredients.

In one embodiment, a combination of osmogens and osmopolymers is used in the osmotic controlled release device.

The core further comprises pharmaceutically acceptable excipients comprising buffer substances such as sodium bicarbonate, binders such as hydroxypropylcellulose, hydroxypropylmethylcellulose and/or polyvinylpyrrolidone, lubricants such as magnesium stearate, wetting agents such as sodiumlauryl sulphate and/or flow regulators such as colloidal silicon dioxide.

Materials for forming the semipermeable membrane of the osmotic controlled release device include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Preferably, the material for forming the semipermeable membrane comprises plasticized, unplasticized, and reinforced cellulose acetate (CA), cellulose diacetate, cellulose triacetate, CA propionate, cellulose nitrate, cellulose acetate butyrate (CAB), CA ethyl carbamate, CA phthalate, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxlated ethylenevinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural and synthetic waxes.

In a further embodiment, the semipermeable membrane may also be a hydrophobic microporous membrane which is permeable to water vapor, as disclosed in U.S. Pat. No. 5,798,119. Hydrophobic polymers for forming hydrophobic but water-permeable membranes comprise polyalkenes, polyethylene, polypropylene, polytetrafluoro-ethylene, polyacrylic acid derivatives, polyethers, polysulfones, polyethersulfones, polystyrenes, polyvinyl halides, polyvinylidene fluoride, polyvinyl esters and ethers, natural and synthetic waxes.

The delivery port(s) on the semipermeable membrane are formed post-coating by mechanical or laser drilling. Alternatively, delivery port(s) are formed in situ by erosion of a plug of water-soluble material or by rupture of a thinner portion of the membrane over an indentation in the core. Yet further, delivery ports are formed during the coating process, as in the case of asymmetric membrane coatings.

The osmotic controlled release dosage form can be prepared according to conventional methods and techniques known to those skilled in the art (see Santus and Baker, J Controlled Release 1995, 35, 1-21; Verma et al., Drug Development and Industrial Pharmacy 2000, 26, 695-708; Verma et al., J Controlled Release 2002, 79, 7-27).

As described above, the dosage form disclosed herein can be an AMT controlled release dosage form, which comprises an asymmetric osmotic membrane that coats a core comprising ketamine and other pharmaceutically acceptable excipients or carriers. (See U.S. Pat. No. 5,612,059 and WO 2002/17918.) The AMT controlled release dosage forms can be prepared according to conventional methods and techniques known to those skilled in the art, including direct compression, dry granulation, wet granulation, and a dip-coating method.

In further embodiments, the dosage form disclosed herein is formulated as ECS controlled release dosage form, which comprises an osmotic membrane that coats a core comprising ketamine, hydroxylethyl cellulose, and other pharmaceutically acceptable excipients or carriers.

In a preferred embodiment of the invention, the oral dosage form is a multi particulate dosage form and comprises a multitude of particles. Particles may be pellets, granules, spheroids, microtablets. Preferably, particles are pellets which contain a core comprising ketamine or a pharmaceutically acceptable salt or solvate thereof.

Preferably, the pellets contain a core comprising ketamine and a release control layer coated upon the core. Preferably, the release control layer is (physically) separated from the ketamine containing core. The ketamine containing core may be a core which contains ketamine and excipients. In those embodiments, the excipients preferably do not substantially retard or delay the release of the ketamine.

Preferably, the core comprises a layer of ketamine on an inert core. The inert core (also referred to as seed core or neutral bead) may be granules or beads, preferably spherical, and further preferably made from sugar or cellulose or other suitable materials. By way of example, spherical inert cores based on saccharose, such as those commercially available under the trade name Suglets® or those based on cellulose, such as those commercially available under the trade name Celphere® or Cellets® may be mentioned. Saccharose-based inert cores are particularly preferred. Inert cores may preferably have a particle size in the range of 100 to 500 µm and more preferably in the range of 200 to 400 µm, with the particle size range indicating the size range for 90% of the particles as determined by sieve analysis.

Preferably, ketamine is provided by coating a ketamine-containing layer directly onto the inert cores. The ketamine-containing layer preferably does not delay release of ketamine, i.e. is an immediate-release layer.

In one embodiment, each pellet contains a core comprising ketamine and a release control layer coated upon the core. In an alternative embodiment, pellets containing ketamine cores and a release control layer coated upon the cores can be mixed to other pellets.

In an embodiment of the invention, the core does not comprise a neutral bead as described above, but a bead comprising ketamine and optionally at least one pharmaceutically acceptable excipient. The ketamine containing bead can be formed by dry granulation, wet granulation, spray granulation or extrusion.

Preferably, a suitable ketamine-containing core comprises
10 to 50 wt. %, preferably 15 to 40 wt. %, more preferably 20 to 30 wt. % inert core (neutral bead),
20 to 90 wt. %, preferably 35 to 80 wt. %, more preferably 50 to 70 wt. % ketamine, in particular ketamine hydrochloride,
0.1 to 20 wt. %, preferably 1 to 15 wt. %, more preferably 3 to 10 wt. % binder, and optionally
0 to 20 wt. %, preferably 1 to 15 wt. %, more preferably 3 to 10 wt. % glidant, based on the total weight of the ketamine containing core.

Binders generally serve to enhance the integrity and stability of tablets. In addition, they may improve the suitability of pharmaceutical compositions for granulation. Binders are commonly also used for the preparation of films, such as active agent containing layers, around an inert core. Exemplary binders include synthetic polymers, such as polyvinyl pyrrolidone (PVP), vinyl pyrrolidone-vinyl acetate-copolymer, modified celluloses, such as hydroxy alkyl celluloses and mixtures thereof. A binder is typically used in an amount of 0 to 25% by weight, preferably 0.1 to 15% by weight and in further embodiments 1 to 10% by weight of the controlled release oral dosage form. Preferably, hypromellose (HPMC) or PVP is used as binder in the ketamine-containing core, more preferably HPMC. Preferably, said HPMC has a methoxy content of 20% to 40%, more preferably 25% to 35%. Further, preferably said HPMC has a hydroxypropoxy content of about 5% to 15%, more preferably 7% to 12%. Preferably, a 2% by weight (aqueous) solution of said HPMC has a viscosity of 0.5 to 100 mPa·s, preferably 1 to 50 mPa·s, more preferably 2 to 10 mPa·s, measured at 20° C., preferably by means of a Brookfield-Synchro-Lectric LVF viscosimeter. Preferably, the PVP has an average molecular weight of 1,000 to 2,500,000, preferably 5,000 to 2,000,000, more preferably 10,000 to 1,500,000.

Generally, glidants such as disperse silica, such as Aerosil®, or talc can be used. In particular, talc is used as glidant in the ketamine-containing core.

In one embodiment, the ketamine-containing core does not comprise a glidant.

The release control layer may be disposed in direct vicinity, i.e. in immediate contact with and surrounding the ketamine containing core, which is preferred. In other exemplary embodiments, an intermediate layer may be disposed between the ketamine containing core and the release control layer. This intermediate layer may further control the release of ketamine from the core. However, it is preferred that, if present, the intermediate layer does not substantially influence the release from the core.

The release control layer comprises a release control substance for controlling the release of ketamine from the pellets. The release control substance may be any substance known in the art as suitable to control the release of an active substance. Exemplary embodiments of suitable control release substances include cellulose esters, such as cellulose acetate phthalate, polyvinyl pyrrolidone, polyvinyl alcohol, polyvinyl acetate, polyvinyl chloride, nylon, polyamide, polyethylene oxide, polylactide-co-glycolide and mixtures thereof. Further suitable polymers include those selected from alkylcelluloses, in particular cellulose ethers, polymers and copolymers based on acrylate or methacrylate, polymers and copolymers based on acrylic or methacrylic esters and mixtures thereof. Preferably, the release control substance is a water insoluble polymer, preferably an alkyl cellulose. More preferably, the alkyl cellulose is ethyl cellulose.

In exemplary embodiments of the present invention wherein the release control substance is a polymer, said polymer has a weight average molecular weight of 5,000 to 500,0000 g/mol, preferably of 50,000 to 900,000 g/mol, more preferably of 100,000 to 400,000 g/mol, for instance of 140,000 to 300,000 g/mol. The weight average molecular weight is preferably determined by gel permeation chromatography.

In further embodiments, and in addition or in the alternative to one or more of the properties mentioned above, the release control substance, and in particular the polymer, preferably has a solubility in water of less than 20 mg/l, preferably less than 15 mg/l, preferably between 0.001 to 10.0 mg/l. The solubility in water is preferably determined in accordance with European Regulation RL67-548 EWG, Annex V, Chapter A6 (German version referred to and referenced herein).

In further embodiments where a polymer is used as or as part of the release control substance, and in addition or in the alternative to one or more of the properties mentioned above, the polymer has a glass transition temperature of 20 to 220° C., for instance 60 to 150° C. or 90 to 140° C. The glass transition temperature is preferably measured by means of differential scanning calorimetry DSC, preferably using a Mettler Toledo instrument and a preferably applying a heating/cooling rate of 10° C. per minute.

In a particularly preferred embodiment the release-control substance is ethylcellulose having an ethoxyl content of about 30 to 70%, more preferred of about 40 to 60%. Preferably, a 2% by weight (aqueous) solution of ethylcellulose has a viscosity of 5 to 500 mPa·s, preferably 10 to 100 mPa·s, measured at 25° C., preferably by means of a Brookfield-Synchro-Lectric LVF viscosimeter.

In exemplary embodiments, the release control substance is contained in an amount of 0.1 to 80% by weight of the total weight of the pellets in the dosage form, more preferably in amounts of 0.5 to 60% by weight, 10 to 50% by weight, 15 to 40% by weight, of the total weight of the pellets in the dosage form.

Control of the release rate can be adapted by appropriate selection of the control release substance or mixture of such substances, its/their amount, coating thickness, inclusion of further excipients, such as pore formers and/or plasticizers or others.

Further to the release control substance, one or more additional excipients may be used, in particular in a release control layer. A preferred excipient for use with the release control substance, in particular a polymeric release control substance, is a plasticizer and/or a pore builder and/or glidants.

A plasticizer, as the term is used herein, is a substance that typically lowers the glass transition temperature of the polymer it is used in admixture with by at least 2° C., preferably at least 5° C., for instance between 5 and 30° C., as compared to the polymer alone. Preferably, the plasticizer is triethyl citrate or propylene glycol.

A pore former usually is a substance having a water-solubility which is higher than the water solubility of the release-control substance. Preferably, the pore former has a solubility in water of more than 20 mg/l, preferably 50 mg/l to 5000 mg/l, more preferably 100 to 1000 mg/l. The solubility in water is preferably determined as described above. In particular, hydroxypropyl cellulose (HPC) is used as pore former.

In a preferred embodiment, the release control layer comprises
20 to 95 wt. %, preferably 40 to 80 wt. %, more preferably 50 to 70 wt. % release control substance, preferably as described above,
0.1 to 30 wt. %, preferably 1 to 25 wt. %, more preferably 5 to 20 wt. % pore builder, preferably as described above,
0.1 to 30 wt. %, preferably 1 to 25 wt. %, more preferably 5 to 20 wt. % plasticizer, preferably as described above, and optionally
0 to 40 wt. %, preferably 3 to 30 wt. %, more preferably 5 to 20 wt. % glidant, preferably as described above,
based on the total weight of the release control layer.

The release control layer may be a single layer or a plurality of layers. For ease of fabrication, embodiments with a single release control layer are preferred.

The pellets may be used as a pharmaceutical formulation, for instance, without any further processing. For this kind of administration, the pellets are preferably filled into sachets. In the alternative, they may be incorporated into capsules, optionally together with one or more excipients, or into other suitable ingestible pharmaceutical dosage forms.

Most preferably, the pellets are contained in an external phase of at least one pharmaceutically acceptable excipient. Furthermore, the controlled release oral dosage form is preferably a tablet.

As evident from what has been set out before, most preferably, the oral dosage form according to the present invention does not contain any ketamine in immediate-release form, i.e. does not contain ketamine, the release of which is not controlled by the release-control substance(s). For instance, a tablet comprising the plurality of controlled release ketamine pellets does not comprise any further ketamine in the external phase or as top-coating on the tablet.

In particularly preferred embodiments, the pellets are mixed to a so-called "external phase" in order to be compressed into tablets. The external phase should ensure the stability of the pellets during the compression and is usually composed of one or more pharmaceutically acceptable excipients, such as fillers, binders, disintegrants, glidants and lubricants.

Fillers are normally used to dilute a pharmaceutical composition and provide bulk. Examples for preferred fillers include lactose, starch, calcium phosphate, calcium carbonate, saccharose, sugar alcohols such as mannitol, sorbitol, xylitol, and celluloses and derivatives. Microcrystalline cellulose is particularly preferred.

In a preferred embodiment a filler mixture comprising sodium carboxymethyl cellulose and microcrystalline cellulose, preferably in a weight ratio of 5:1 to 1:5, more preferably 3:1 to 1:3 is used. A filler or mixture of fillers may be used in an amount of 0 to 80% by weight, preferably 1 to 70% by weight, based on the total weight of the controlled release oral dosage form, preferably the tablet.

Binders generally serve to enhance the integrity and stability of tablets. In addition, they may improve the suitability of pharmaceutical compositions for granulation. Binders are commonly also used for the preparation of films, such as active agent containing layers, around an inert core. Exemplary binders include synthetic polymers, such as polyvinyl pyrrolidone, vinyl pyrrolidone-vinyl acetate-co-polymer, modified celluloses, such as hydroxy alkyl celluloses and mixtures thereof. A binder is typically used in an amount of 0 to 30% by weight, preferably 0.1 to 15% by weight and in further embodiments 1 to 10% by weight of the controlled release oral dosage form. Preferably hypromellose (HPMC) is used as binder.

A disintegrant enhances the disintegration of a dosage form, in particular a tablet, after its immersion in water or gastric juices. Suitable disintegrants include carrageenan, starchs, croscarmellose, crospovidone and mixtures thereof. Disintegrants may be used in amounts of 0 to 25% by weight, preferably 1 to 20% by weight and in further embodiments 3 to 15% by weight of the controlled release oral dosage form, preferably the tablet.

The oral dosage forms may further include a glidant, such as disperse silica, such as Aerosil®, or talc. A glidant (or mixture thereof) may be comprised in an amount of 0 to 5% by weight, for instance 0.1 to 4% by weight of the controlled release oral dosage form, preferably the tablet.

The oral controlled release dosage form may further comprise a lubricant, in particular in tablets prepared by compression. Suitable lubricants include stearic acid, magnesium stearate, adipic acid and sodium stearyl fumarate (Pruv®).

Preferably, the amount of pellets in the controlled release oral dosage form ranges from 1% to 100% by weight, based on the total weight of the controlled release dosage form. In preferred embodiments, the pellets are comprised in an amount of 20% to 90% by weight, more preferably 25% to 80% by weight, based on the total weight of the controlled release dosage form.

In a preferred embodiment the external phase (without coated cores) comprises
85 to 99.9%, preferably 90 to 98% by weight filler,
0 to 5%, preferably 0.1 to 1.0% by weight lubricant and
0.1 to 10%, preferably 1.0 to 5% by weight glidant,
based on the total weight of the external phase.

Optionally, the oral dosage form according to the present invention, particularly when present in the form of a tablet, can comprise an external film for improved ease of swallowing, for protection, for colouring, for taste-masking or other purposes. Preferably, this external film does not influence the release of ketamine to any significant extent. The external film may comprise the usual excipients known in this art for this purpose. A combination of hypromellose, talc, a colouring agent, such as titanium dioxide, and/or a polymer, such as polyethylene glycol is a preferred embodiment herein. Preferably, ready to use products like Opadry® based on hypromellose or polyvinyl alcohol are used for the film coating. This optional film is not counted towards the total weight of the controlled release oral dosage form herein. Expressed differently, any amount of an ingredient expressed as weight percent herein refers to the controlled release oral dosage form without this optional external film. As evident from the above, the external film is free of ketamine in any form.

The oral dosage form according to the present invention has the advantage that it may be divided into two or more units without impairing the controlled release of ketamine. The controlled release oral dosage form, and in particular the tablet, may therefore comprise means facilitating its division into two or more units, such as a break-line, each of said units providing controlled release of ketamine. The dosage form according to the present invention therefore provides for the possibility to adjust the dosage, for instance halve the dosage by breaking the tablet in two.

In preferred embodiments according to the present invention, the ketamine salt is ketamine hydrochloride. The dosage form may contain ketamine in amounts of 5 to 400 mg, preferably 5 to 200 mg. If ketamine is used as free base, the amount of 5 to 400 mg refers to the weight of the free base. If ketamine is used in the form of a pharmaceutical acceptable salt, the amount of 5 to 400 mg refers to the weight of the salt. Preferably, the dosage form of the present invention comprises 10 mg ketamine, 20 mg ketamine, 40 mg ketamine, 80 mg ketamine, 100 mg ketamine, 120 mg ketamine, 140 mg ketamine, 160 mg ketamine, 180 mg ketamine, 200 mg ketamine, 220 mg ketamine, 240 mg ketamine, 260 mg ketamine, 280 mg ketamine, 300 mg ketamine, 320 mg ketamine, 340 mg ketamine, 360 mg ketamine, 380 mg ketamine, more preferably 10 mg ketamine hydrochloride, 20 mg ketamine hydrochloride, 40 mg ketamine hydrochloride, 80 mg ketamine hydrochloride, 100 mg ketamine hydrochloride, 120 mg ketamine hydrochloride, 140 mg ketamine hydrochloride, 160 mg ketamine hydrochloride, 180 mg ketamine hydrochloride, 200 mg ketamine hydrochloride, 220 mg ketamine hydrochloride, 240 mg ketamine hydrochloride, 260 mg ketamine hydrochloride, 280 mg ketamine hydrochloride, 300 mg ketamine hydrochloride, 320 mg ketamine hydrochloride, 340 mg ketamine hydrochloride, 360 mg ketamine hydrochloride, 380 mg ketamine hydrochloride.

It is further preferred that the dosage form of the present invention comprises:
i) ketamine-containing cores comprising
  1 to 30 wt. %, preferably 2 to 20 wt. %, more preferably 3 to 10 wt. % inert cores,
  1 to 40 wt. %, preferably 5 to 20 wt. %, more preferably 10 to 15 wt. % ketamine, in particular ketamine hydrochloride,
  0.01 to 10 wt. %, preferably 0.1 to 5 wt. %, more preferably 0.5 to 3 wt. % binder, and
  0 to 10 wt. %, preferably 0.1 to 5 wt. %, more preferably 0.5 to 3 wt. % glidant,
ii) a release-control layer coated on each ketamine-containing core, comprising
  1 to 40 wt. %, preferably 3 to 20 wt. %, more preferably 7 to 15 wt. % release-control substance,
  0.01 to 10 wt. %, preferably 0.1 to 6 wt. %, more preferably 1 to 4 wt. % pore builder,
  0 to 10 wt. %, preferably 0.1 to 6 wt. %, more preferably 1 to 4 wt. % plasticizer,
  0 to 15 wt. %, preferably 0.1 to 10 wt. %, more preferably 0.5 to 5 wt. % glidant,
and
iii) an external phase comprising
  20 to 85%, preferably 40 to 75%, more preferably 50 to 65% filler,
  0 to 3 wt. %, preferably 0.001 to 2.0 wt. %, more preferably 0.1 to 0.5 wt. % lubricant and
  0 to 5 wt. %, preferably 0.1 to 5 wt. %, more preferably 0.5 to 2.0 wt. % glidant,
wherein all wt. % are based on the total weight of the tablet (without film coating).

The tablets of the present invention preferably have a tablet height of 2 to 8 mm, more preferably 3 to 5 mm, and a length of 3 to 22 mm, preferably 5 to 17 mm Preferably, the tablets have a hardness of 40 to 300 N, more preferably of 50 to 200 N.

In a further embodiment of the invention, the administration of a single oral dosage form leads in-vivo to a $C_{max}$ of ketamine of 1 to 150 ng/ml, preferably 2 to 120 ng/ml, more preferably 3 to 100 ng/ml, still more preferably 4 to 70 ng/ml, further more preferably 5 to 40 ng/ml, and to a $AUC_{0-\infty}$ of 5 to 1000 h·ng/ml, preferably 10 to 750 h·ng/ml, more preferably 50 to 600 h·ng/ml, still more preferably 100 to 400 h·ng/ml.

In a further embodiment, the administration of a single oral dosage form leads in-vivo to a $C_{max}$ of norketamine of 5 to 750 ng/ml, preferably 10 to 600 ng/ml, more preferably 15 to 500 ng/ml, still more preferably 20 to 400 ng/ml, further more preferably 25 to 300 ng/ml, and to a $AUC_{0-\infty}$ of 100 to 8000 h·ng/ml, preferably 150 to 6000 h·ng/ml, more preferably 500 to 4000 h·ng/ml.

"$C_{max}$" means the peak concentration of ketamine in the plasma, e.g. determined as described below. "$AUC_{0-\infty}$" describes ketamine bioavailability and is measured by calculating the area under curve (AUC) of the plasma drug concentration time profile from time zero extrapolated to infinity.

In a further preferred embodiment of the invention, $T_{max}$ of ketamine is 3 to 9 h, preferably 3 to 8 h, more preferably 4 to 7 h, most preferably 5 to 7 h.

In a further preferred embodiment of the invention, $T_{max}$ of norketamine is 3 to 9 h, preferably 3 to 8 h, more preferably 4 to 7 h, most preferably 5 to 7 h.

"$T_{max}$" means the time from administration to reach $C_{max}$.

In a further preferred embodiment of the invention, the oral dosage form has a $F_{abs}$ of 5 to 25%, preferably 7 to 20%, more preferably 9 to 18%.

"$F_{abs}$" is the absolute bioavailability. Absolute bioavailability compares the bioavailability of the active drug in systemic circulation following non-intravenous administration (i.e., after oral administration in the present case), with the bioavailability of the same drug following intravenous administration. It is the fraction of the drug absorbed through non-intravenous administration compared with the corresponding intravenous administration of the same drug. The absolute bioavailability is the dose-corrected area under curve (AUC) non-intravenous (oral) divided by AUC intravenous. For example, the formula for calculating $F_{abs}$ for a drug administered by the oral route is given below:

$$F_{abs} = AUC_{oral}/AUC_{iv} \times dose_{iv}/dose_{oral}$$

The controlled release oral dosage forms according to the present invention are preferably for use in the treatment of severe and very severe pain, more preferably of severe and very severe pain corresponding to a value of between 6 and 10 according to the visual analogue scale (VAS) numeric pain distress scale of 1 to 10. In particular, the controlled release oral dosage form is suitable for patients who need continuous treatment over an extended period of time.

The controlled release oral dosage forms according to the present invention are preferably for use in the treatment of neuropathic pain. As described above, neuropathic pain is found in spinal cord injury, multiple sclerosis, and some strokes. Aside from diabetes and other metabolic conditions, the common causes of painful peripheral neuropathies are herpes zoster infection, HIV-related neuropathies, nutritional deficiencies, toxins, remote manifestations of malignancies, immune mediated disorders and physical trauma to a nerve trunk. Neuropathic pain is common in cancer as a direct result of cancer on peripheral nerves (e.g., compression by a tumor), or as a side effect of chemotherapy, radiation injury or surgery.

Accordingly, the oral dosage form of the present invention is preferably for use in the treatment of patients suffering from spinal cord injury, multiple sclerosis, cancer, immune mediated disorders, metabolic conditions such as diabetes, herpes zoster infection, HIV-related neuropathies, or nutritional deficiencies.

Further, the present invention provides a method for treating severe and very severe pain, more preferably of severe and very severe pain corresponding to a value of between 6 and 10 according to the visual analogue scale (VAS) numeric pain distress scale of 1 to 10, using an oral dosage form of ketamine as described above.

In a further embodiment, a method for treating depression in patients with depression and bipolar disorder who have not responded to antidepressants is provided.

Yet further, a method of treating neuropathic pain is provided using an oral dosage form of ketamine as described above.

In an embodiment of the invention, a method of treating patients suffering from spinal cord injury, multiple sclerosis, cancer, immune mediated disorders, metabolic conditions such as diabetes, herpes zoster infection, HIV-related neuropathies, or nutritional deficiencies using the oral dosage form of the present invention is disclosed.

The oral dosage form of the present invention is administered once or twice daily, preferably twice daily.

According to a further aspect, the present invention provides a method for preparing an oral dosage form, preferably as described above, comprising:
a) coating each inert core with a layer comprising ketamine or a pharmaceutically acceptable salt or solvent thereof,
b) coating each coated inert core with a release control layer comprising a release control substance for controlling the release of ketamine, thus forming pellets,
c) mixing the pellets with at least one pharmaceutically acceptable excipient,
d) forming a tablet from the mixture comprising the pellets and the at least one pharmaceutically acceptable excipient.

For preferred embodiments of inert cores, preferred ketamine forms, release controlling substances, further excipients, the pellets etc., it is referred to the explanations concerning embodiments of the dosage forms of the present invention above, which naturally equally apply to the method for preparing a controlled release dosage form according to the present invention.

Step a) may further include dissolving or suspending ketamine or a salt thereof in a suitable solvent or solvent mixture, optionally together with a binder, such as a hydroxyalkyl cellulose, such as hydroxy propylmethyl cellulose. The solvent is preferably water, an alcohol, such as ethanol, or mixtures thereof.

Preferably, the inert cores are sugar spheres. Preferably, ketamine hydrochloride is used. Further preferably, the coating step a) is a coating step in a fluid bed processor wherein preferably a solution or suspension (in particular solution) of ketamine hydrochloride and one or more excipients, such as hypromellose, is sprayed onto the inert cores. The coating solution or suspension usually comprises respectively consists of water and/or an alcohol. Preferably, the process temperature is between 30 and 60° C.

Preferably, step b) involves coating by spraying a coating solution containing the release control substance onto the coated inert cores from step a). The spraying step is preferably performed in a fluid bed processor. The fluid bed processor is preferably suitable for coating powders, particles, inert spheres, beads and tablets, and/or simultaneous drying. Preferably, the process temperature is between 30 and 60° C.

The solvent of the coating solution or suspension from step b) predominantly contains alcohol, i.e. the solvent used for dissolving the release controlling agent and optional further excipients contains preferably 60% or more by weight, more preferably 70% or more by weight of alcohol. A mixture of ethanol and water is particularly preferred. Furthermore, preferably ethylcellulose is used as the release controlling agent. Additional excipients may include hydroxypropyl cellulose, talc, triethyl citrate and other pharmaceutically suitable excipients.

The pellets preferably have a weight average particle diameter ($d_{50}$) of 50 to 1000 µm, in preferred embodiments 100 to 800 µm, in further embodiments 150 to 600 µm, as measured by sieve analysis, such as by means of a Retsch Siebmaschine AS 300 control. The thickness of the release control layer is preferably in a range of 0.1 to 200 µm, preferably 0.5 to 100 µm.

Tablets with a combination of several of the above features have been found to be particularly advantageous: they provide good clinical efficacy, not least due to providing an advantageous dissolution profile without the need to include an immediate release portion of ketamine They can be broken or divided without affecting the release of drug from the tablet. Dose dumping phenomena do not occur.

BRIEF DESCRIPTION OF THE DRAWINGS

The invention will be further described by way of exemplary embodiments with reference to the Figure wherein.

EXAMPLES

Example 1: Preparation of Matrix Controlled Release Tablets Containing 20 mg Ketamine Hydrochloride

| | |
|---|---|
| Ketamine HCl | 20.00 mg |
| Hydrogenated castor oil | 92.74 mg |
| Microcrystalline cellulose | 35.00 mg |
| Aerosil 200 | 1.50 mg |
| Magnesium stearate | 0.76 mg |
| Total tablet | 150.00 mg |

Ketamine HCl, hydrogenated castor oil, microcrystalline cellulose and Aerosil 200 are sieved through a 600 µm sieve and mixed for 10 minutes.

Magnesium stearate is added to the mixture and further mixed for 2 minutes. Tablets with the composition outlined in the table above are pressed on a rotary machine with oblong punches.

Example 2: Preparation of Multi-Particulate Tablets Containing 20 mg Ketamine Hydrochloride Step 1:
A spraying solution is prepared from the following ingredients:

| | |
|---|---|
| Hypromellose | 3.00 kg |
| Ketamine hydrochloride | 20.00 kg |
| Sugar spheres | 8.00 kg |
| Ethanol 96% | q.s. |
| Water, purified | q.s. |

A spraying suspension is prepared by successively dissolving hypromellose and ketamine hydrochloride in a mixture of purified water and ethanol.

Sugar spheres (saccharose, particle size range (90%) 200 to 400 µm) are filled into a fluid-bed processor with a bottom-spray nozzle and pre-heated. The spraying suspension is then sprayed onto the sugar spheres in the fluid-bed processor, thus preparing a plurality of sugar spheres having a layer of ketamine coated thereupon. The coated sugar spheres are then sieved to remove agglomerates (vibration sieve or equivalent).

Step 2:

A coating suspension is prepared from the following ingredients:

| | |
|---|---|
| Ethylcellulose | 14.54 kg |
| Hydroxypropyl cellulose | 4.00 kg |
| Triethyl citrate | 3.27 kg |
| Talc | 1.45 kg |
| Ethanol 96% | q.s |
| Water, purified | q.s |

Hydroxypropyl cellulose is dissolved in water. Ethylcellulose and ethanol are then added to the solution. Finally, triethyl citrate and talc are added and the solution is continuously stirred.

The coated sugar spheres from Step 1 are filled into a fluid-bed processor and preheated. The coated solution prepared as indicated above is sprayed onto the coated sugar spheres. The pellets obtained thereby as then sieved to remove the agglomerates.

Step 3:

The following ingredients are dry mixed to a blend:

| | |
|---|---|
| Pellets from Step 2 | 54.26 kg |
| Carmellose sodium | 46.00 kg |
| Microcrystalline cellulose | 55.49 kg |
| Colloidal anhydrous silica | 1.50 kg |
| Magnesium stearate | 0.75 kg |

The resulting dry blend is then compressed to tablets.

Step 4 (Optional):

A tablet coating suspension is made from the following ingredients:

| | |
|---|---|
| Opadry ® II White | 1.20 kg |
| Water, purified | q.s |

31.6 kg tablets are film coated with the tablet coating suspension.

Figure 1:
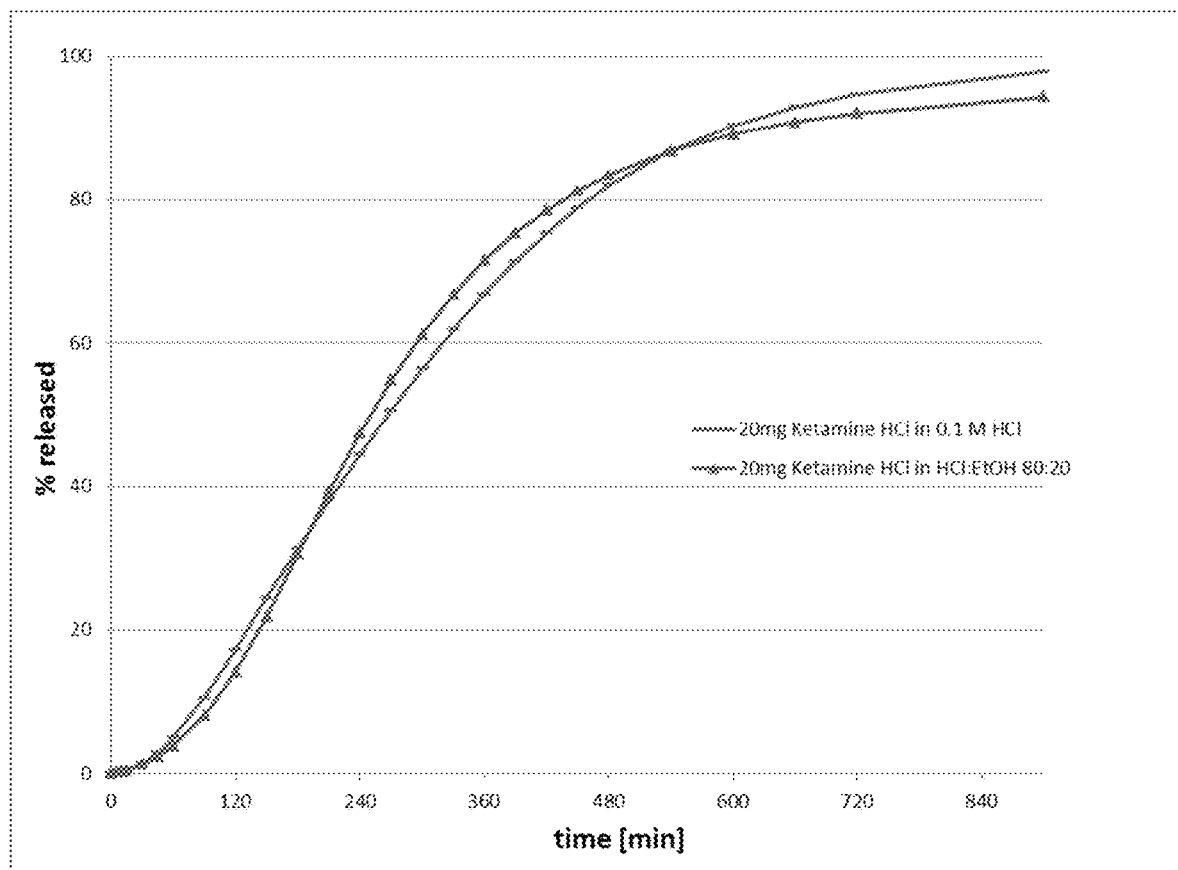
FIG. 1 shows the dissolution profiles of a 20 mg containing ketamine hydrochloride tablet in 0.1M HCl and of a 20 mg containing ketamine hydrochloride tablet in HCl/EtOH 80:20.
Figure 2A:
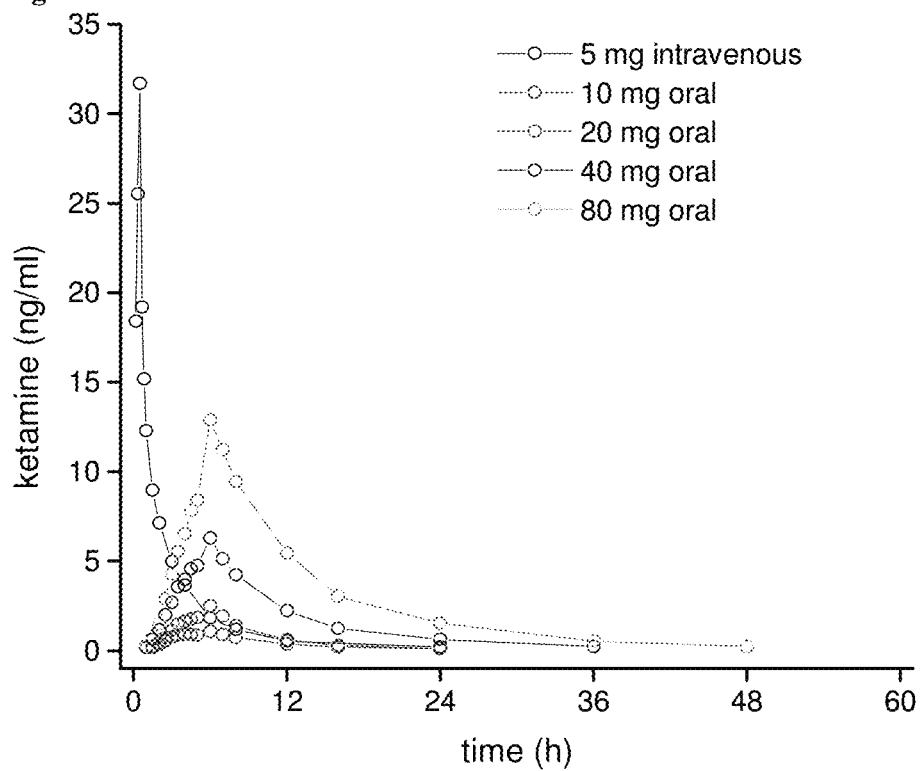
FIG. 2a shows the geometric mean curves of (±)-ketamine after i.v. infusion of 5 mg (within 0.5 h) and oral administration of 10, 20, 40 and 80 mg ketamine modified release tablets according to the invention.
Figure 2B:
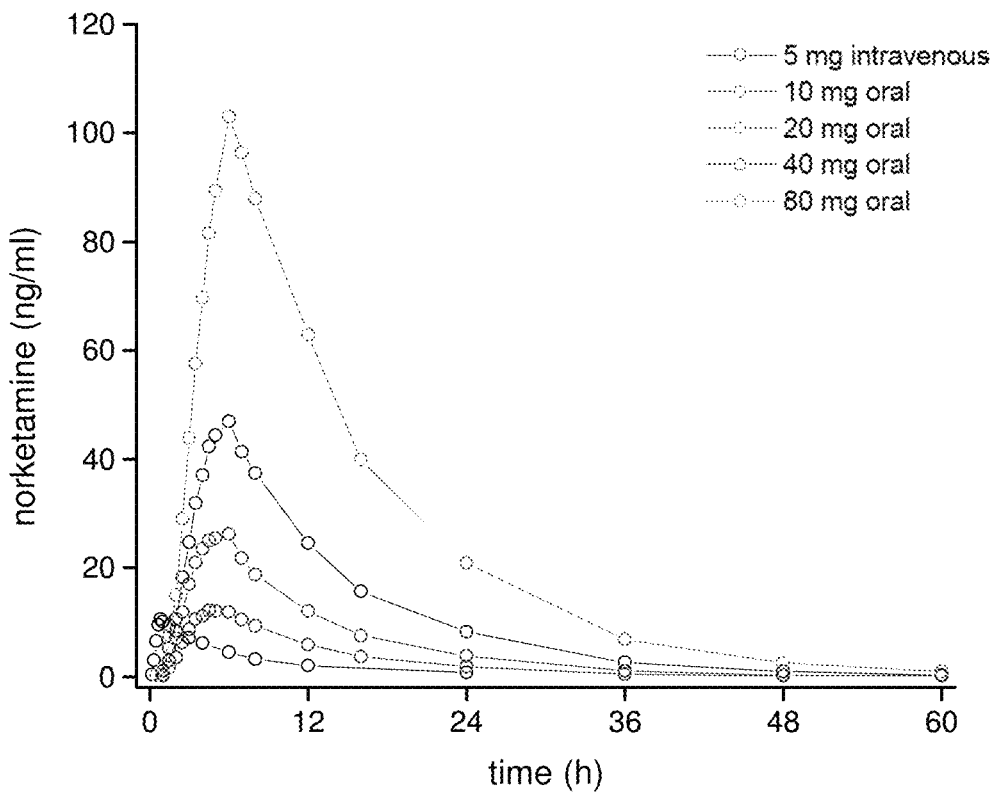
FIG. 2b shows the geometric mean curves of (±)-norketamine after i.v. infusion of 5 mg (within 0.5 h) and oral administration of 10, 20, 40 and 80 mg ketamine modified release tablets according to the invention.

The dissolution profiles of the 20 mg tablets are in accordance with the present invention, as apparent from FIG. 1. The dissolution profiles were measured using the USP 1 Basket Method at 37° C., 1000 ml 100 rpm in 0.1M HCl and HCl/EtOH 80:20.

Example 3: In Vivo Pharmacokinetics

A comparative bioavailability study of ketamine and norketamine after single dose administration of ketamine (in form of ketamine hydrochloride) 10, 20, 40 and 80 mg modified release tablets according to the invention in fasting state and 5 mg ketamine (in form of ketamine hydrochloride) solution for infusion was carried out. In the study, the $C_{max}$, $F_{abs}$, $AUC_{0-\infty}$ and $T_{max}$ as described above are determined in vivo in healthy subjects.

The modified release tablets have been produced in analogy to Example 2.

Objectives

Single dose, open label, five-treatment, five-period, consecutive study with at least 7 days wash-out between the study periods.

In the first treatment all subjects received a single dose of 5 mg (±)-ketamine solution for infusion within 30 min intravenously in fasting state.

The orally administered single doses of (±)-ketamine modified release tablets were given in consecutively increasing doses of 10, 20, 40 and 80 mg with 240 ml of table water in fasting state.

(±)-Ketamine and (±)-norketamine were measured in serum, urine and feces

Number of Subjects, Main Criteria for Inclusion 15 analyzed age: 18-45 years sex: male and female ethnic origin: Caucasian body mass index: ≥18.5 kg/m² and ≤30 kg/m² good health as evidenced by the results of the clinical examination, ECG, and the laboratory check-up, which were judged by the clinical investigator not to differ in a clinical relevant way from the normal state heart frequency between 50 and 90 bpm blood pressure between 140 and 100 systolic and 90 and 60 diastolic written informed consent Sampling Blood: blank, 0.167, 0.333, 0.5, 0.667, 0.833, 1, 1.5, 2, 3, 4, 6, 8, 12, 24 h after intravenous administration and blank, 0, 0.5, 1, 1.5, 2, 2.5, 3, 3.5, 4, 4.5, 5, 6, 7, 8, 12, 16, 24, 36, 48, 60 h after oral administration Urine: 0-24 h, 24-48 h and 48-72 h Feces: 0-120 h Drug Assay Validated achiral LC-MS/MS method for (±)-ketamine and (±)-norketamine, performed in a laboratory certified according to GLP (Good Laboratory Practice)

Pharmacokinetic Results

The results are summarized in the following tables, wherein $AUC_{0-\infty}$ stands for the area under the curve from zero extrapolated to infinity, $C_{max}$ stands for the maximum plasma concentration, $T_{max}$ stands for the time to $C_{max}$, $F_{abs}$ stands for absolute bioavailability, $T_{1/2}$ stands for the apparent terminal half-life.

TABLE 1

Pharmacokinetic characteristics of (±)-ketamine after intravenous infusion (30 min) of 5 mg (±)-ketamine and oral administration of 10, 20, 40 and 80 mg ketamine PR tablets

| | | 5 mg i.v. | 10 mg | 20 mg | 40 mg | 80 mg |
|---|---|---|---|---|---|---|
| $AUC_{0-\infty}$ | ng × h/ml | 59.9 ± 13.2 | 13.5 ± 9.73 | 27.1 ± 21.9 | 75.6 ± 48.3 | 178 ± 145 |
| $C_{max}$ | ng/ml | 33.7 ± 9.74 | 1.48 ± 0.901 | 3.25 ± 2.29 | 7.64 ± 4.69 | 16.7 ± 13.4 |
| $T_{max}$ | h | — | 4.87 ± 1.22 | 5.87 ± 0.64* | 6.00 ± 0.76* | 6.07 ± 0.26* |

TABLE 1-continued

Pharmacokinetic characteristics of (±)-ketamine after intravenous infusion (30 min) of 5 mg (±)-ketamine and oral administration of 10, 20, 40 and 80 mg ketamine PR tablets

|  |  | 5 mg i.v. | 10 mg | 20 mg | 40 mg | 80 mg |
|---|---|---|---|---|---|---|
| $F_{abs}$ | % | — | 11.5 ± 8.09 | 11.0 ± 8.57 | 15.9 ± 9.53*† | 17.9 ± 12.3*† |
| $T_{1/2}$ | h | 6.99 ± 5.22 | 7.39 ± 4.86 | 6.09 ± 4.98 | 8.44 ± 1.54#† | 8.89 ± 1.42#† | vs. 5 mg i.v.,
*vs. 10 mg,
†vs 20 mg

TABLE 2

Pharmacokinetics of (±)-norketamine after intravenous infusion (30 min) of 5 mg (±)-ketamine and oral administration of 10, 20, 40 and 80 mg ketamine PR tablets

|  |  | 5 mg | 10 mg | 20 mg | 40 mg | 80 mg |
|---|---|---|---|---|---|---|
| $AUC_{0-\infty}$ | ng × h/ml | 87.7 ± 24.1 | 162 ± 39.7 | 339 ± 100 | 653 ± 164 | 1620 ± 731 |
| $C_{max}$ | ng/ml | 11.4 ± 2.85 | 13.4 ± 2.92 | 27.6 ± 6.62 | 48.7 ± 10.4 | 113 ± 53.0 |
| $T_{max}$ | h | 0.93 ± 0.32 | 4.72 ± 1.02 | 5.33 ± 0.77* | 5.67 ± 0.52* | 6.10 ± 0.60*†‡ |
| $T_{1/2}$ | h | 8.01 ± 2.35 | 7.38 ± 1.63 | 7.74 ± 3.09 | 8.25 ± 2.70† | 8.48 ± 1.56* |

*vs. 10 mg,
†vs 20 mg,
‡vs. 40 mg,
p < 0.05 (Wilcoxon test)

The maximum concentration ($C_{max}$) and the time of maximum concentration ($T_{max}$) were obtained directly from the measured concentration-time curves.

The area under the concentrations-time curve (AUC0-t) was calculated with the measured data points from the time of administration until the last quantifiable concentration by the trapezoidal formula. The AUC was assessed up to the last sampling time above the limit of quantification and is extrapolated to infinity to obtain the $AUC_{0-\infty}$ values.

Apparent Terminal half-life ($T_{1/2}$) was calculated by the following equation $T_{1/2} = \ln 2/\lambda_z$. The terminal elimination rate constant ($\lambda_z$) was evaluated from the terminal slope by log-linear regression analysis.

The absolute bioavailability ($F_{abs}$) was calculated by the following equation $$F_{abs} = AUC_{oral}/AUC_{iv} \times dose_{iv}/dose_{oral}.$$

The invention claimed is:

1. A method for treating depression in patients with depression and bipolar disorder who have not responded to antidepressants and to avoid dose dumping upon ingestion of alcohol, said method comprising orally administering an oral dosage form to a subject in need of such treatment, said oral dosage form comprising ketamine or a pharmaceutically acceptable salt or solvate thereof, wherein the dosage form provides an in vitro release of ketamine, when measured according to the USP Basket Method I in 0.1M HCl at 37° C. at 100 rpm, of 0 to 40% after 2 hours, of 10 to 70% after 4 hours, of 30 to 85% after 6 hours and of 45 to 100% after 8 hours,
wherein the dosage form provides an in vitro release of ketamine, when measured according to the USP 1 Basket Method in 0.1M HCl at 100 rpm, after one hour at 37° C., in an aqueous solution containing 20% by volume of ethanol, in a ratio of less than 2:1 relative to the amount of ketamine released, so measured, after one hour at 37° C. in an ethanol-free aqueous solution,
wherein the dosage form is a multi-particulate controlled release dosage form, wherein the dosage form comprises pellets containing a core comprising ketamine or a pharmaceutically acceptable salt or solvate thereof, and a release control layer comprising a release control substance coated upon the core, wherein the release control substance is a water insoluble polymer, and
wherein the pellets are contained in an external phase of at least one pharmaceutically acceptable excipient.

2. The method according to claim 1, wherein the core comprises a layer comprising ketamine coated on an inert core.

3. The method according to claim 1, wherein the release control substance is an alkyl cellulose.

4. The method according to claim 1, wherein the release control substance is ethylcellulose.

5. The method according to claim 1, wherein the external phase comprises carboxymethyl cellulose, optionally in the form of a salt, as a pharmaceutically acceptable excipient.

6. The method according to claim 1 wherein the oral dosage form is a tablet.

7. The method according to claim 1, wherein the ketamine salt is ketamine hydrochloride and wherein the amount comprised in the oral dosage form is in the range of from 5 to 400 mg ketamine hydrochloride.

8. The method according to claim 1, wherein the dosage form is administered once or twice daily.

9. The method according to claim 1 wherein the oral dosage form is a multi-particulate tablet, wherein the tablet comprises
i) ketamine-containing cores comprising
1 to 30 wt. % inert beads,
1 to 40 wt. % ketamine,
0.01 to 10 wt. % binder, and
0 to 10 wt. % glidant,
ii) a release-control layer coated on each ketamine-containing core, comprising
1 to 40 wt. % release-control substance,
0.01 to 10 wt % pore builder,
0.01 to 10 wt. % plasticizer,
0 to 15 wt. % glidant,
and
iii) an external phase comprising
20 to 85 wt. % filler,
0 to 3 wt. % lubricant and
0 to 5 wt. % glidant,
wherein all wt. % are based on the total weight of the tablet.

10. The method according to claim 1, wherein the administration of a single oral dosage form leads in vivo to a $C_{max}$ of ketamine of 1 to 150 ng/ml and to a $AUC_{0-\infty}$ of 5 to 1000 h·ng/ml.

11. The method according to claim 1, wherein $T_{max}$ of ketamine is 3 to 9 h.

12. The method according to claim 1 wherein the oral dosage form has an absolute bioavailability $F_{abs}$ of 5 to 25%.

13. The method according to claim 1, wherein the subject is suffering from spinal cord injury, multiple sclerosis, cancer, immune mediated disorders, metabolic conditions, herpes zoster infection, HIV-related neuropathies, or nutritional deficiencies.

14. The method according to claim 1, wherein the oral dosage form is prepared by:
 a) coating inert cores with a layer comprising ketamine or a pharmaceutically acceptable salt or solvent thereof,
 b) coating the coated inert cores with a release-control layer comprising the release-controlling substance, thus forming pellets,
 c) mixing the pellets with at least one pharmaceutically acceptable excipient,
 d) forming a tablet from the mixture comprising the pellets and the at least one pharmaceutically acceptable excipient.

15. A method for treating depression in patients with depression and bipolar disorder who have not responded to antidepressants and to avoid dose dumping upon ingestion of alcohol, said method comprising orally administering an oral dosage form to a subject in need of such treatment, said oral dosage form comprising ketamine or a pharmaceutically acceptable salt or solvate thereof, wherein the dosage form provides an in vitro release of ketamine, when measured according to the USP Basket Method I in 0.1M HCl at 37° C. at 100 rpm, of 0 to 40% after 2 hours, of 10 to 70% after 4 hours, of 30 to 85% after 6 hours and of 45 to 100% after 8 hours,
 wherein the dosage form provides an in vitro release of ketamine, when measured according to the USP 1 Basket Method in 0.1M HCl at 100 rpm, after one hour at 37° C., in an aqueous solution containing 20% by volume of ethanol, in a ratio of less than 2:1 relative to the amount of ketamine released, so measured, after one hour at 37° C. in an ethanol-free aqueous solution,
 wherein the dosage form is a multi-particulate controlled release tablet, wherein the tablet comprises pellets containing a core comprising ketamine or a pharmaceutically acceptable salt or solvate thereof, and a release control layer comprising a release control substance coated upon the core, wherein the release control substance is a water insoluble polymer,
 wherein the core comprises
  1 to 30 wt. % inert beads,
  1 to 40 wt. % ketamine,
  0.01 to 10 wt. % binder, and
  0 to 10 wt. % glidant,
 wherein the release-control layer comprises
  1 to 40 wt. % release-control substance,
  0.01 to 10 wt % pore builder,
  0.01 to 10 wt. % plasticizer,
  0 to 15 wt. % glidant,
 wherein the pellets are contained in an external phase of at least one pharmaceutically acceptable excipient,
 wherein the external phase comprises
  20 to 85 wt. % filler,
  0 to 3 wt. % lubricant and
  0 to 5 wt. % glidant,
 wherein the external phase comprises carboxymethyl cellulose, optionally in the form of a salt, as a pharmaceutically acceptable excipient, and
 wherein all wt. % are based on the total weight of the dosage form.

16. An oral dosage form comprising ketamine or a pharmaceutically acceptable salt or solvate thereof for use in the treatment of depression in patients with depression and bipolar disorder who have not responded to antidepressants, and to avoid dose dumping upon ingestion of alcohol,
 wherein the dosage form provides an in vitro release of ketamine, when measured according to the USP I Basket Method in 0.1M HCl at 37° C. at 100 rpm of 0 to 40% after 2 hours, of 10 to 70% after 4 hours, of 30 to 85% after 6 hours and of 45 to 100% after 8 hours,
 wherein the dosage form provides an in vitro release of ketamine, when measured according to the USP I Basket Method in 0.1M HCl at 100 rpm, after one hour at 37° C., in an aqueous solution containing 20% by volume of ethanol, in a ratio of less than 2:1 relative to the amount of ketamine released, so measured, after one hour at 37° C. in an ethanol-free aqueous solution,
 wherein the dosage form is a matrix controlled release dosage form or a multi particulate controlled release dosage form,
 wherein in said matrix controlled release dosage form ketamine is dissolved or dispersed in an inert matrix and is released by diffusion through the inert matrix once administered, and
 wherein said multi particulate controlled release dosage form comprises pellets containing a core comprising ketamine and a release control layer coated upon the core.

* * * * *